United States Patent

Wagner et al.

[11] Patent Number: 5,350,751
[45] Date of Patent: Sep. 27, 1994

[54] SUBSTITUTED IMIDAZOLES, PHARMACEUTICAL COMPOSITIONS CONTAINING THESE, AND THE USE THEREOF AS ANTAGONISTS OF ANGIOTENSIN II RECEPTORS FOR THE TREATMENT OF HIGH BLOOD PRESSURE

[75] Inventors: Adalbert Wagner, Hofheim am Taunus; Rainer Henning, Hattersheim am Main; Hermann Gerhards, Hofheim am Taunus; Bernward Schölkens, Kelkheim/Taunus, all of Fed. Rep. of Germany; Jean-Paul Vevert, Pantin; Jean-Claude Caille, Angers, both of France

[73] Assignee: Hoechst Aktiengesellschaft, Frankfurt am Main, Fed. Rep. of Germany

[21] Appl. No.: 679,233

[22] Filed: Apr. 2, 1991

[30] Foreign Application Priority Data

Apr. 4, 1990 [DE] Fed. Rep. of Germany ....... 4010797

[51] Int. Cl.$^5$ .............. C07D 233/57; C07D 401/02; C07D 403/02; C07D 405/02; C07D 407/02; A61K 311/415
[52] U.S. Cl. ..................... 514/258; 514/300; 514/375; 514/381; 514/397; 544/281; 546/121; 548/235; 548/252; 548/254; 548/311.4; 548/312.1
[58] Field of Search ............... 546/121; 514/300, 258, 514/375, 381, 397; 544/281; 548/235, 252, 254, 311.4, 312.1

[56] References Cited

U.S. PATENT DOCUMENTS 3,555,040  1/1971  Frick et al. ................... 514/394
4,355,040  10/1982  Furukawa et al. ............ 548/336

FOREIGN PATENT DOCUMENTS 0028834  5/1981  European Pat. Off. .
0054233  6/1982  European Pat. Off. .
0253310  1/1988  European Pat. Off. .
0323841  7/1989  European Pat. Off. .
0324377  7/1989  European Pat. Off. .

Primary Examiner—Floyd D. Higel
Attorney, Agent, or Firm—Finnegan, Henderson, Farabow, Garrett & Dunner

[57] ABSTRACT

The invention relates to compounds of the formula I

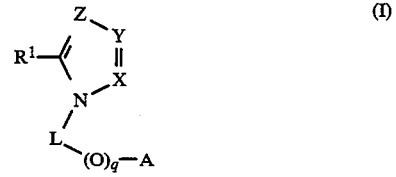

in which X, Y and Z are identical or different and are N or CR$^2$, R$^1$ and R$^2$ are as defined in the description, L is an alkylene radical, q is 0 or 1, and A is the radical of a fused heterobicyclic compound. The invention furthermore relates to a process for preparing the said compounds, agents containing these, and the use thereof in the treatment of high blood pressure.

20 Claims, No Drawings

SUBSTITUTED IMIDAZOLES, PHARMACEUTICAL COMPOSITIONS CONTAINING THESE, AND THE USE THEREOF AS ANTAGONISTS OF ANGIOTENSIN II RECEPTORS FOR THE TREATMENT OF HIGH BLOOD PRESSURE

DESCRIPTION

Substituted azoles, processes for the preparation thereof, agents containing these, and the use thereof EP-A-324377, EP-A-253310, EP-A-28834, which corresponds to U.S. Pat. No. 3,555,040 issued Jan. 12, 1971, and EP-A-323841 disclose derivatives of imidazole, pyrrole, pyrazole and triazole and the use thereof as antagonists of angiotensin II receptors.

Novel compounds of the azole type have now been found and are, surprisingly, highly active antagonists of angiotensin II receptors both in vitro and in vivo.

The invention relates to compounds of the formula I

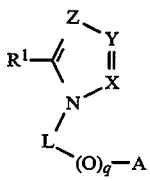

in which
a) X, Y and Z are identical or different and are N or $CR^2$,
b) $R^1$ is
1. $(C_2-C_{10})$-alkyl,
2. $(C_3-C_{10})$-alkenyl,
3. $(C_3-C_{10})$-alkynyl,
4. $OR^3$,
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $-(CH_2)_m-B-(CH_2)_n-R^4$,
10. benzyl,
11. a radical which is defined as under b) 1., 2., 3. or 9. and is monosubstituted with $CO_2R^3$,
12. a radical which is defined as under b) 1., 2., 3. or 9. and in which 1 to all hydrogen atoms are replaced by fluorine, or
13. the radical which is defined under b) 10. and is substituted on the phenyl by 1 or 2 identical or different radicals from the series comprising halogen, $(C_1-C_4)$-alkoxy and nitro;
c) $R^2$ is
1. hydrogen,
2. halogen,
3. nitro,
4. $C_vF_{2v+1}$,
5. pentafluorophenyl,
6. cyano,
7. phenyl,
8. phenyl-$(C_1-C_3)$-alkyl,
9. $(C_1-C_{10})$-alkyl,
10. $(C_3-C_{10})$-alkenyl,
11. phenyl-$(C_2-C_6)$-alkenyl,
12. 1-imidazolyl-$(CH_2)_m-$,
13. 1,2,3-triazolyl-$(CH_2)_n-$,
14. tetrazolyl-$(CH_2)_m-$,
15. $-(CH_2)_{o-1}-CHR^7-OR^5$,
16. $-(CH_2)_o-O-CO-R^3$,
17. $-(CH_2)_o-S-R^6$,
18. $-S(O)_r-R^6$,
19. $-CH=CH-(CH_2)_m-CHR^3-OR^6$,
20. $-CH_2=CH-(CH_2)_m-CO-R^8$,
21. $-CO-R^8$,
22. $-CH=CH-(CH_2)_m-O-CO-R^7$,
23. $-(CH_2)_m-CH(CH_3)-CO-R^8$,
24. $-(CH_2)_o-CO-R^8$, 25. 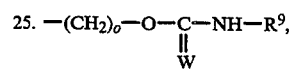

26. 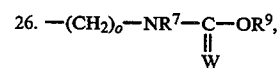

27. $-(CH_2)_o-NR^7-CO-NHR^9$,
28. $-(CH_2)_o-NR^7-SO_2R^9$,

29. 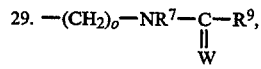

30. $-(CH_2)_nF$,
31. $-(CH_2)_n-O-NO_2$,
32. $-CH_2-N_3$,
33. $-(CH_2)_n-NO_2$,
34. $-CH=N-NR^5R^7$,
35. phthalimido-$(CH_2)_n-$, 36. 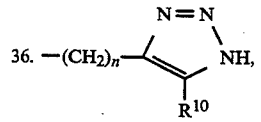

37. 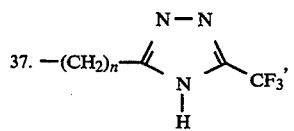

38. 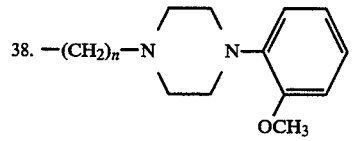

39. 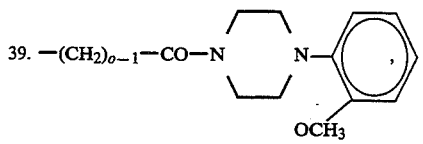

40. phenyl-$SO_2-NH-N=CH-$,

41. 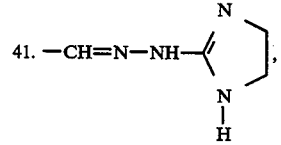

42. $-(CH_2)_n-SO_2-NR^7-CO-NR^6R^9$,
43. $-(CH_2)_o-SO_2R^9$, 44. a radical which is defined as under c) 7. or 8. and which is substituted on the phenyl by 1 or 2 identical or different radicals from the series comprising halogen, hydroxyl, methoxy, trifluoromethyl, $CO_2R^3$ and phenyl,
45. a radical which is as defined under c) 9., 10. or 18. and in which 1 to all hydrogen atoms have been replaced by fluorine, or
46. the radical which is defined under c) 13. and which is substituted by 1 or 2 identical or different radicals from the series comprising methoxycarbonyl and $(C_1-C_4)$-alkyl;

d) $R^3$ is
  1. hydrogen,
  2. $(C_1-C_8)$-alkyl,
  3. $(C_3-C_8)$-cycloalkyl,
  4. phenyl,
  5. benzyl or
  6. the radical which is defined under d) 2. and in which 1 to all hydrogen atoms have been replaced by fluorine;

e) $R^4$ is
  1. hydrogen,
  2. $(C_1-C_6)$-alkyl,
  3. $(C_3-C_8)$-cycloalkyl,
  4. $(C_2-C_4)$-alkenyl or
  5. $(C_2-C_4)$-alkynyl;

f) $R^5$ is
  1. hydrogen,
  2. $(C_1-C_6)$-alkyl,
  3. $(C_3-C_8)$-cycloalkyl,
  4. phenyl or
  5. benzyl;

g) $R^6$ is
  1. hydrogen,
  2. $(C_1-C_6)$-alkyl,
  3. $(C_3-C_8)$-cycloalkyl,
  4. $(C_6-C_{12})$-aryl, preferably phenyl,
  5. benzyl,
  6. $(C_1-C_9)$-heteroaryl which can be partially or completely hydrogenated, preferably 2-pyrimidinyl
  7. $(C_1-C_4)$-alkanoyl,
  8. a radical which is defined as under g) 4. or 6. and is substituted by 1 or 2 identical or different radicals from the series comprising halogen, hydroxyl, methoxy, nitro, cyano, $CO_2R^3$ and trifluoromethyl, $NR^{11}R^{12}$ or

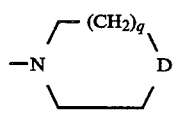

9. $(C_1-C_9)$-heteroaryl-$(C_1-C_3)$-alkyl, it being possible for the heteroaryl moiety to be partially or completely hydrogenated;

h) $R^7$ is
  1. hydrogen,
  2. $(C_1-C_6)$-alkyl,
  3. $(C_3-C_8)$-cycloalkyl,
  4. $(C_6-C_{12})$-aryl-$(C_1-C_6)$-alkyl, preferably benzyl,
  5. phenyl or
  6. $(C_1-C_9)$-heteroaryl;

i) $R^8$ is
  1. hydrogen,
  2. $(C_1-C_6)$-alkyl,
  3. $(C_3-C_8)$-cycloalkyl,
  4. phenyl-$(CH_2)_q$—,
  5. $OR^5$,
  6. $NR^{11}R^{12}$ or 7. 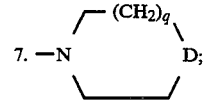

j) $R^9$ is
  1. $(C_1-C_6)$-alkyl,
  2. 1-adamantyl,
  3. 1-naphthyl,
  4. 1-naphthylethyl,
  5. phenyl-$(CH_2)_q$— or
  6. the radical which is defined under j) 1. and in which 1 to all hydrogen atoms have been replaced by fluorine;

k) $R^{10}$ is cyano, nitro or $CO_2R^7$;

l) $R^{11}$ and $R^{12}$ are identical or different and are
  1. hydrogen,
  2. $(C_1-C_4)$-alkyl,
  3. phenyl,
  4. benzyl or
  5. α-methylbenzyl;

m) D is $NR^{13}$, O or $CH_2$;

n) $R^{13}$ is hydrogen, $(C_1-C_4)$-alkyl or phenyl;

o) A is a fused heterobicyclic radical which has 8 to 10 ring atoms, of which up to 9 ring atoms are carbon atoms, and which can be substituted by up to 6, preferably up to 3, identical or different radicals $R^{14}$ or —$(CH_2)_{n-1}$—$(CHR^6$—$CH_2)_{o-1}$—$R^{15}$;

$R^{14}$ is
  1. halogen,
  2. oxo,
  3. nitroso,
  4. nitro,
  5. amino,
  6. cyano,
  7. hydroxyl,
  8. $(C_1-C_6)$-alkyl,
  9. $(C_1-C_4)$-alkanoyl,
  10. $(C_1-C_1)$-alkanoyloxy,
  11. $CO_2R^3$,
  12. methanesulfonylamino,
  13. trifluoromethanesulfonylamino,
  14. —CO—NH—$OR^9$,
  15. —$SO_2$—$NR^6R^7$,
  16. —$CH_2$—$OR^7$,
  17. $(C_1-C_9)$-heteroaryl-$(CH_2)_q$—, preferably 1-tetrazolyl,
  18. $(C_7-C_{13})$-aroyl;

19. —$CH_2$—N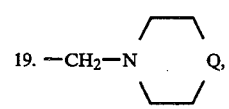Q,

20. —$(CH_2C)_o$—N〈 〉Q or

21. $(C_6—C_{12})$-aryl;

q) $R^{15}$ is
  1. hydrogen,

2. $(C_1-C_6)$-alkyl,
3. $(C_3-C_8)$-cycloalkyl,
4. $(C_6-C_{12})$-aryl,
5. $(C_7-C_{13})$-aroyl,
6. $(C_1-C_4)$-alkoxy,
7. $(C_1-C_4)$-alkanoyloxy,
8. $(C_1-C_9)$-heteroaryl,
9. $CO_2R^3$,
10. halogen,
11. cyano,
12. nitro,
13. $NR^6R^7$,
14. hydroxyl,
15. —CO—NH—$CHR^5$—$CO_2R^3$,
16. sulfo,
17. —$SO_3R^3$,
18. —$SO_2$—$NR^7$—CO—$NR^6R^9$,
19. —$NR^7$—CO—$NR^6$—$SO_2$—$CH_2$—$R^5$,
20. —$C(CF_3)_2OH$,
21. phosphonooxy,
22. —$PO_3H_2$,
23. —NH—$PO(OH)_2$,
24. —$S(O)_rR^6$,
25. —CO—$R^8$,
26. —CO—$NR^6R^9$,
27. —$CR^{20}(OH)$—$PO(OH)_2$,
28. the radical defined under p) 20., 29. 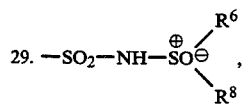

30. 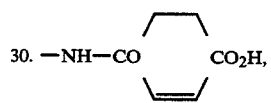

31. 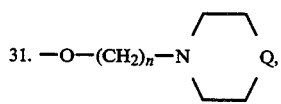

32. 5-tetrazolyl-NH—CO—,
33. —CO—NH—NH—$SO_2CF_3$,

34. 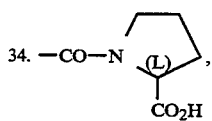

35. 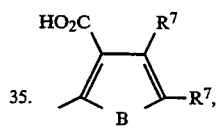

36. 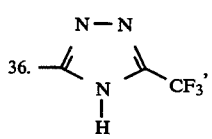

37. 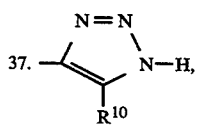

38. 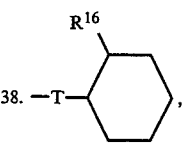

39. 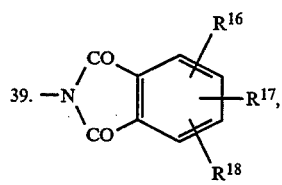

40. —CO—NH—$SO_2$—$R^{19}$ or
41. the radical which is defined under q) 4. and substituted by 1 or 2 identical or different radicals from the series comprising halogen, cyano, nitro, $NR^6R^7$ and hydroxyl;

r) B is O, $NR^7$ or S;
s) W is O or S;
t) L is $(C_1-C_3)$-alkanediyl;
u) $R^{16}$ is $CO_2R^3$ or $CH_2CO_2R^3$;
v) $R^{17}$ is hydrogen, halogen, $(C_1-C_4)$-alkyl or $(C_1-C_4)$-alkoxy;
w) $R^{18}$ is hydrogen, $(C_1-C_4)$-alkyl or phenyl;
x) $R^{19}$ is
1. $(C_1-C_8)$-alkyl,
2. $(C_3-C_8)$-cycloalkyl,
3. phenyl,
4. benzyl or
5. the radical which is defined under x) 1. and in which 1 to all hydrogen atoms are replaced by fluorine or chlorine;
y) T is
1. a single bond,
2. —CO—,
3. —$CH_2$—,
4. —O—,
5. —S—,
6. —$NR^{21}$—,
7. —CO—$NR^{21}$,
8. —$NR^{21}$—CO—,
9. —O—$CH_2$—,
10. —$CH_2$—O—,
11. —S—$CH_2$—,
12. —$CH_2$—S—,
13. —NH—$CR^{20}R^{21}$—,
14. —$NR^{21}$—$SO_2$—,
15. —$SO_2$—$NR^{21}$—,
16. —$CR^{20}R^{22}$—NH—,
17. —CH=CH—,
18. —CF=CF—,
19. —CH=CF—,
20. —CF=CH—,
21. —$CH_2$—$CH_2$—,
22. —$CF_2$—$CF_2$—,
23. —$CH(OR^3)$—,
24. —$CH(OCOR^5)$—,
25. $-\overset{\underset{\|}{NR^{23}}}{C}-$ or 26. 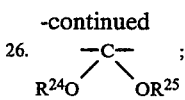

z) R[20] and R[22] are identical or different and are hydrogen, ($C_1$–$C_5$)-alkyl, phenyl, allyl or benzyl;
a') R[21] is hydrogen, ($C_1$–$C_6$)alkyl, benzyl or allyl;
b') R[23] is
 1. NR[20]R[21],
 2. ureido,
 3. thioureido,
 4. toluene-4-sulfonyl or
 5. benzenesulfonylamino;
c') R[24] and R[25] are identical or different and are ($C_1$–$C_4$)-alkyl or together are —$(CH_2)_q$—;
d') Q is $CH_2$, NH, O or S;
e') m is an integer from 0 to 5;
f') n is an integer from 1 to 5;
g') o is an integer from 1 to 10;
h') q is 0 or 1;
i') r is 0, 1 or 2, or
j') v is an integer from 1 to 6;
and the physiologically tolerated salts thereof.

Alkyl, alkenyl and alkynyl can be straight-chain or branched. A corresponding statement applies to radicals derived therefrom, such as alkanoyl or alkoxy.

Cycloalkyl, preferably ($C_3$–$C_8$)-cycloalkyl, may, optionally, be substituted with alkyl groups.

($C_6$–$C_{12}$)-Aryl is, for example, phenyl, naphthyl or biphenylyl, preferably phenyl. A corresponding statement applies to radicals derived therefrom, such as aroyl or aralkyl.

($C_1$–$C_9$)-Heteroaryl means, in particular, radicals which are derived from phenyl or naphthyl and in which one or more CH groups are replaced by N and/or in which at least two adjacent CH groups are replaced by S, NH or O (with the formation of a five-membered aromatic ring). It is also possible for one or both atoms at the point of fusion of bicyclic radicals (as in indolizinyl) to be a nitrogen atom.

Examples of these are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

The fused heterobicyclic compound AH, from which the radical A is derived, means, in particular, a bicyclic ring system which has 8 to 10 ring atoms, of which up to 9 ring atoms are carbon atoms and in which two adjacent atoms are constituents common to both rings. One or both of these rings are formally derived from benzene in which one or more CH groups are replaced by N, $O^+$ and $S^+$ and/or in which two adjacent CH groups are replaced by S, NH or O (with the formation of a five-membered aromatic ring). A is, for example, a radical of benzothiophene, benzofuran, indole, isoindole, indazole, benzimidazole, quinoline, isoquinoline, phthalazine, quinoxaline, quinazoline, cinnoline, benzothiazole, benzothiazole 1,1-dioxide, coumarin, chroman, benzoxazole, benzisothiazole, benzodiazines, benzotriazole, benzotriazine, benzoxazine, imidazopyridine, imidazopyrimidine, imidazopyrazine, imidazopyridazine, imidazothiazole, pyrazolopyridine, thienopyridine and pyrrolopyrimidine. The said heterobicyclic compound AH can also be partially or completely hydrogenated. However, one ring of AH preferably remains aromatic, in which case a benzo-fused heterobicyclic compound AH is particularly preferred.

In the case of sulfur-containing and/or partially saturated radicals, the bicyclic compound can also be, for example, oxo-substituted, as is the case with the radical of benzo-1,2,3-triazinone.

A is linked either by the isocyclic or by the heterocyclic moiety by an alkanediyl bridge L.

Physiologically tolerated salts of compounds of the formula I mean both organic and inorganic salts thereof, as are described in Remington's Pharmaceutical Sciences, 17th edition, page 1418 (1985). On the basis of physical and chemical stability and solubility, preferred for acid groups are, inter alia, sodium, potassium, calcium and ammonium salts; for basic groups inter alia salts with hydrochloric acid, sulfuric acid, phosphoric acid, carboxylic acids or sulfonic acids, such as acetic acid, citric acid, benzoic acid, maleic acid, fumaric acid, tartaric acid and p-toluenesulfonic acid.

Preferred compounds of the formula I are those in which
a) X is N, Y is CR[2] and Z is CR[2];
b) X is CR[2], Y is N and Z is CR[2];
c) X is CR[2], Y is CR[2] and Z is N or
d) X, Y and Z are each N.

Further preferred compounds of the formula I are those in which
a) R[1] is
 1. ($C_3$–$C_{10}$)-alkyl,
 2. ($C_3$–$C_{10}$)-alkenyl,
 3. ($C_3$–$C_{10}$)-alkynyl,
 4. ($C_3$–$C_8$)-cycloalkyl,
 5. benzyl or
 6. benzyl which is substituted as defined in claim 1;
b) R[2] is
 1. hydrogen,
 2. halogen,
 3. nitro,
 4. $C_vF_{2v+1}$,
 5. pentafluorophenyl,
 6. cyano,
 7. phenyl,
 8. phenyl-($C_1$–$C_3$)-alkyl,
 9. ($C_1$–$C_{10}$)-alkyl,
 10. ($C_3$–$C_{10}$)-alkenyl,
 11. phenyl-($C_2$–$C_6$)-alkenyl,
 12. 1-imidazolyl-$(CH_2)_m$—,
 13. 1,2,3-triazolyl-$(CH_2)_o$—,
 14. tetrazolyl-$(CH_2)_m$—,
 15. —$(CH_2)_{o-1}$—CHR[7]—OR[5],
 16. —$(CH_2)_o$—O—COR[3],
 17. —COR[8],
 18. —$(CH_2)_o$—CO—R[8],
 19. —$S(O)_r$R[6],
 20. —CH=CH—$(CH_2)_m$—CHR[3]—OR[6],
 21. —$CH_2$=CH—$(CH_2)_m$—CO—R[8],
 22. —$(CH_2)_o$—NH—CO—OR[9],
 23. —$(CH_2)_o$—NH—$SO_2$—R[9],
 24. —$(CH_2)_n$F,
 25. —$(CH_2)_o$—$SO_3$R[9],
 26. —$(CH_2)_n$—$SO_2$—NH—CO—NR[6]R[9] or
 27. a radical which is as defined under b) 7., 8., 9., 10. or 13. and which is substituted as defined above under c) 46., 45. or 44. in each case as described for a radical of this type;
c) R[8] is hydrogen; ($C_1$–$C_5$)-alkyl, OR[5], NR[11]R[12] or morpholino;
d) T is 1. a single bond,
2. —CO—,
3. —CONR$^{21}$—,
4. —CH$_2$—CH$_2$—,
5. —NR$^{21}$—CO—,
6. —O—CH$_2$—,
7. —CH$_2$—O—,
8. —S—CH$_2$—,
9. —CH$_2$—S—,
10. —NH—CH$_2$—,
11. —CH$_2$—NH— or
12. —CH=CH— and the other radicals and variables are as defined above.

Particularly preferred compounds of the formula I are those in which a) R$^1$ is (C$_3$–C$_7$)-alkyl, (C$_3$–C$_7$)-alkenyl or (C$_3$–C$_7$)-alkynyl;

b) R$^2$ is
1. chlorine,
2. bromine,
3. C$_v$F$_{2v+1}$ with v=1, 2 or 3,
4. pentafluorophenyl,
5. —S(O)$_r$R$^6$,
6. (CH$_2$)$_{o-1}$—CHR$^7$—OR$^5$,
7. (CH$_2$)$_o$—O—CO—R$^3$,
8. —COR$^8$,
9. —(CH$_2$)$_o$—CO—R$^8$,
10. —CH$_2$—NH—CO—R$^8$,
11. —(CH$_2$)$_o$—NH—SO$_2$—R$^9$,
12. —CH=CH—CHR$^3$—OR$^6$,
13. tetrazolyl-(CH$_2$)$_m$—,
14. —(CH$_2$)$_n$SO$_2$—NH—CO—NR$^6$R$^9$,
15. —(CH$_2$)$_o$—SO$_3$R$^9$ or optionally hydroxyl-substituted (C$_1$–C$_6$)-alkyl, preferably hydroxymethyl;

c) R$^3$ is hydrogen or (C$_1$–C$_4$)-alkyl;

d) R$^6$ is hydrogen, (C$_1$–C$_4$)-alkyl, (C$_1$–C$_4$)-alkanoyl, a radical which is as defined above under g) 4., 6. or 9. and is substituted by 1 or 2 identical or different radicals from the series comprising halogen, hydroxyl, methoxy, nitro, cyano, CO$_2$R$^3$ and trifluoromethyl, or (C$_1$–C$_9$)-heteroaryl, preferably 2-pyrimidyl;

e) R$^7$ is hydrogen, (C$_1$–C$_4$)-alkyl, (C$_1$–C$_9$)-heteroaryl or (C$_6$–C$_{12}$)-aryl-(C$_1$–C$_4$)-alkyl;

f) R$^8$ is hydrogen, (C$_1$–C$_4$)-alkyl, OR$^5$ or morpholino;

g) R$^9$ is CF$_3$, (C$_1$–C$_6$)-alkyl or phenyl;

h) R$^{14}$ is
1. (C$_1$–C$_4$)-alkyl,
2. (C$_1$–C$_4$)-alkoxy,
3. cyano,
4. amino,
5. nitroso,
6. nitro,
7. fluorine,
8. chlorine,
9. bromine,
10. hydroxyl,
11. CH$_2$OR$^7$,
12. (C$_1$–C$_9$)-heteroaryl-CH$_2$—,
13. (C$_1$–C$_4$)-alkanoyloxy,
14. (C$_1$–C$_4$)alkanoyl,
15. benzoyl,

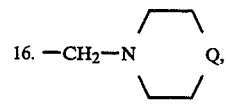

17. —NH—CO—R$^7$ or
18. tetrazolyl;

i) R$^{15}$ is
1. (C$_1$–C$_4$)-alkyl
2. (C$_6$–C$_{12}$)-aryl,
3. (C$_1$–C$_3$)-alkanoyloxy
4. (C$_1$–C$_4$)-alkoxy,
5. (C$_1$–C$_9$)-heteroaryl, preferably 5-tetrazolyl,
6. cyano,
7. nitro,
8. hydroxyl,
9. —S(O)$_r$R$^6$,
10. —SO$_3$R$^3$,
11. chlorine,
12. bromine,
13. benzoyl,
14. —CO$_2$R$^3$,
15. —CO—NH—R$^6$,
16. —NR$^6$R$^7$,
17. —CO—R$^8$,
18. —SO$_2$—NR$^6$R$^7$,

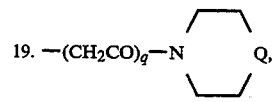

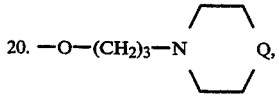

21. —SO$_2$—NH—CO—NR$^6$R$^9$,
22. —PO$_3$H,
23. —CO—CHR$^5$—CO$_2$H,
24. —NH—CO—NH—SO$_2$—CH$_2$—R$^5$,
25. 5-tetrazolyl-NH—CO—,

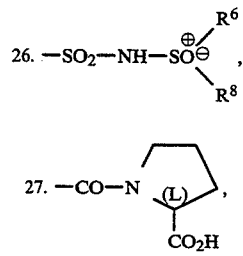

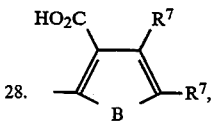

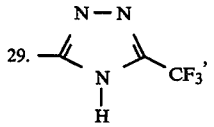

30. 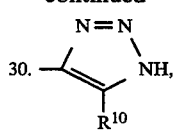

31. 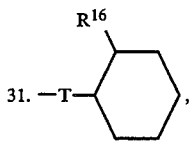

32. 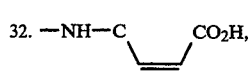

33. 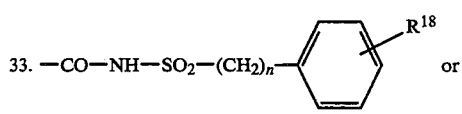 or 34. the radical which is defined under i) 2. and is substituted as defined above;

j) Q is $CH_2$, NH or O;
k) $R^{18}$ is hydrogen, methyl or ethyl;
l) T is a single bond, —O—, —CO—, —NHCO— or —$OCH_2$—;

and the remaining radicals and variables are as defined above.

Compounds of the formula (I) where the symbols $R^2$, $R^9$, $R^{14}$, $R^{15}$, Z, X, Y, L and q have the following meanings:

a) $R^2$ is chlorine, bromine, —$S(O)_rR^6$, —$COR^8$ or —$(CH_2)_nSO_2$—NH—CO—$NR^6R^9$;
b) $R^9$ is ($C_1$-$C_6$)-alkyl;
c) $R^{14}$ is tetrazolyl;
d) $R^{15}$ is —$CO_2$—$R^3$, —$SO_2$—$NR^6R^7$, —$SO_2$—N-H—CO—$NR^6R^9$ or —NH—CO—N-H—$SO_2$—$CH_2$—$R^5$;
e) Z is N;
f) X and Y are both $CR_2$;
g) q is zero; and p1 h) L is $CH_2$;

are very particularly preferred.

The invention also relates to a process for preparing compounds of the formula I, which comprises alkylating compounds of the formula II

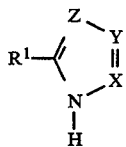    (II)

in which $R^1$, X, Y and Z are as defined above, with compounds of the formula III U-L-(O)$_q$-A    (III)

in which L, A and q are as defined above, and U is a leaving group, where appropriate eliminating again protective groups which have been temporarily introduced, and converting the resulting compounds of the formula I, where appropriate, into the physiologically tolerated salts thereof.

Suitable leaving groups U are preferably nucleofugic groups (cf. Angew. Chem. 72 [1960]71) such as halogen, o-toluenesulfonate, mesylate or triflate.

Processes for preparing the precursors of the formula II are disclosed in, inter alia, U.S. Pat. No. 4,355,044, EP-A-324,377 and EP-A-323,841.

Other processes are described in G. L'abbe, Chem. Rev. 69, 345 (1969); T. Srodsky in "The Chemistry of the Azido Group", Wiley, N.Y., 1971, page 331; H. Wamhoff in "Comprehensive Heterocyclic Chemistry", S. Katritzky Ed., Pergamon Press, New York (1984).

Suitable for the alkylation of the azoles of the formula II are, for example, appropriate benzyl halides, tosylates, mesylates or triflates or appropriate alkyl halides, tosylates, mesylates or triflates.

The synthesis of these derivatives, such as benzofurans, benzothiophenes and indoles with benzylic $CH_3$ group, has been described by, inter alia, R. P. Dickson et al. in J. Med. Chem. 29, 1637 (1986), and ibid. 29, 1643 (1986). Suitable hydroxybenzotriazoles can be prepared by the method of R. Geiger et al., Chem. Ber. 103, 788 (1970). The preparation of benzoimidazoles, benzothiazoles, benzodiazines, benzopyrones, benzothiazolones, benzotriazines, benzoxazines, benzoxazoles is outlined in the edition cited above "Comprehensive Heterocyclic Chemistry", S. Katritzky Ed. Pergamon Press, New York (1984). It was possible to obtain other heterocyclic compounds by the methods of E. Abignente et al. in J. Heterocyclic Chem. 26, 1875 (1989), A. Krubsack et al. in J. Org. Chem. 41, 3399 (1976) and of F. Santer et al. in Mh. Chem. 99, 715 (1968).

The alkylation is carried out in an analogous manner by processes known in principle.

The azole derivative of the formula II is metallated in the presence of a base, for example. Preferred bases are metal hydrides of the formula MH such as, for example, lithium, sodium or potassium hydride in, for example, DMF or DMSO as solvents or metal alkoxides of the formula MOR, where R is methyl, ethyl or t-butyl, and the reaction is carried out in the corresponding alcohol, DMF or DMSO. The salts of the azoles formed in this way are dissolved in an aprotic solvent such as DMF or DMSO, and a suitable amount of alkylating reagent is added.

An alternative possibility for the deprotonation of the azole derivatives is, for example, reaction with potassium carbonate in DMF or DMSO.

The reactions are carried out at temperatures below room temperature up to the boiling point of the reaction mixture, preferably between +20° C. and the boiling point of the reaction mixture, for about 1 to 10 hours.

The compounds of the formula I according to the invention have an antagonistic action on angiotensin II receptors and can therefore be used for treating hypertension which is dependent on angiotensin II. Additional possible uses are for cardiac insufficiency, cardioprotection, myocardial infarct, cardiac hypertrophy, arteriosclerosis, nephropathy, kidney failure and vascular disorders of the brain such as transient ischemic attacks and stroke.

Renin is a proteolytic enzyme which belongs to the class of aspartyl proteases and which is secreted as a consequence of various stimuli (volume depletion, sodium deficiency, β-receptor stimulation) by the juxtaglomerular cells of the kidney into the blood circulation. There it cleaves the decapeptide angiotensin I off the angiotensinogen which is secreted by the liver. The former is converted by angiotensin converting enzyme (ACE) into angiotensin II. Angiotensin II plays an essential part in the regulation of blood pressure because it increases the blood pressure directly by vasoconstriction. In addition, it stimulates the secretion of aldosterone from the adrenal and, in this way, increases, via inhibition of sodium excretion, the extracellular fluid volume which, in turn, contributes to an increase in blood pressure.

Post-receptor effects are, inter alia, stimulation of phosphoinositol turnover ($Ca^{2+}$ release), activation of protein kinase C, and facilitation of cAMP-dependent hormone receptors.

The affinity of compounds of the formula I for the angiotensin II receptor can be determined by measuring the $_{125}$I-angiotensin II or $^3$H-angiotensin II displacement from receptors on zona glomerulosa membranes of bovine adrenals. The dissected membranes are suspended in buffer at pH 7.4 for this purpose. In order to prevent degradation of the radioligand during the incubation, aprotinin, a peptidase inhibitor, is added. Additionally used are approximately 14,000 cpm of a tracer with a specific activity of 74 TBq/mmol (commercially available from Amersham Buchler) and an amount of receptor protein which binds 50% of the tracer. The reaction is started by adding 15 µl of membrane suspension to a mixture of 100 µl of buffer+aprotinin; 50 µl of buffer with or without angiotensin II or receptor antagonist and 50 µl of tracer. After an incubation time of 60 minutes at 25° C., bound and free radioligand are separated by a filtration assay with Whatmann ® GFIC filters on a Skatron ® cell collector.

Non-specific binding is prevented by treating the filters with 0.3% polyethyleneimine pH=10 (Sigma, No. 3143). The strength of the displacement of the radioligand from the receptor is determined by measuring the radioactivity in a gamma scintillation counter. The $IC_{50}$ values, which are the concentrations of the inhibitor needed to displace 50% of the ligand, are determined by the method of Chem. et al. J. Theor. Biol. 59, 253 (1970). For the compounds of the formula (I) they are in the range $1 \times 10^{-4} - 1 \times 10^{-9}$ M.

To determine the antagonistic effect of the compounds of the formula (I), it is possible to measure their effect on the increase in blood pressure induced by angiotensin II in anesthetized Sprague-Dawley rats. The anesthetic used is sodium thiobarbital (Trapanal ®, Byk Gulden) in an i.p. dosage of 100 mg/kg. The i.v. administration takes place into the jugular vein. The blood pressure is measured in the carotid artery. The animals are firstly pretreated with pentolinium tartrate (10 mg/kg i.m.) so that a lower blood pressure level is reached (ganglion blockade). ANG II (Hypertensin ®, CIBA) is administered i.v. in the volume of 0.1 ml/100 g in 10-minute intervals. The dose is 0.5 µg/kg. The compounds of the formula (I) are dissolved in distilled water and administered intravenously or intraduodenally in the dosages 0.1-1; 10 and 100 mg/kg.

The compounds of the formula (I) are active in the range 0.1-100 mg/kg.

The invention likewise relates to pharmaceutical compositions composed of a compound of the formula I and other active substances such as, for example, diuretics or nonsteroidal anti-inflammatory active substances. The compounds of the formula I can also be used as diagnostic aids for the renin-angiotensin system.

Pharmaceutical products contain an effective amount of the active substance of the formula I and, possibly, other active substances together with an inorganic or organic pharmaceutically utilizable excipient. Intranasal, intravenous, subcutaneous or oral use is possible.

The dosage of the active substance depends on the warm-blooded species, the body weight, age and on the mode of administration.

The pharmaceutical products of the present invention are prepared in dissolving, mixing, granulating or coating processes known per se.

For a form for oral use, the active compounds are mixed with the additives customary for this purpose, such as excipients, stabilizers or inert diluents, and converted by customary methods into suitable dosage forms; such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. This preparation can be both as dry and wet granules. Examples of suitable oily excipients or solvents are vegetable or animal oils, such as sunflower oil and fish liver oil.

For subcutaneous or intravenous administration, the active compounds or the physiologically tolerated salts thereof are converted, if desired with the substances customary for this purpose, such as solubilizers, emulsifiers or other auxiliaries into solutions, suspensions or emulsions. Examples of suitable solvents are: water, physiological saline solutions or alcohols, for example ethanol, propanediol or glycerol, as well as sugar solutions such as glucose or mannitol solutions, or else a mixture of the various solvents mentioned.

List of abbreviations:
DMF N,N-dimethylformamide
NBS N-bromosuccinimide
AIBN α,α-azobis-isobutyronitrile
EI electron impact
DCI desorption chemical ionization
RT room temperature
EA ethyl acetate (EtOAc)
DIP diisopropyl ether
H n-heptane

EXAMPLE 1

1-[(2-Carboxy-benzo[b]furan-5-yl)methyl]-2-butyl-4-chloro-5-hydroxymethyl-imidazole a) Ethyl 5-methylbenzo[b]furan-2-carboxylate 12 g (0.088 mol) of 2-hydroxy-5-methylbenzaldehyde are dissolved in 150 ml of abs. DMF. 14.6 g of potassium carbonate (0.105 mol) are added, followed by 9.5 g (0.088 mol) of ethyl chloroacetate dropwise. After 3 hours under reflux, the mixture is diluted with 500 ml of $H_2O$, extracted 3× with ethyl acetate, washed 4× with water, dried with magnesium sulfate and concentrated. Chromatography on $SiO_2$ with ethyl acetate/cyclohexane (1:5) yields 7.6 g of oil.

MS (EI)=204 (M+) $R_f$[$SiO_2$; EtOAc/cyclohexane (1:4)]=0.41 b) Ethyl 5-bromomethylbenzo[b]furan-2-carboxylate 7.6 g (37 mmol) of the compound from a) are boiled under reflux with 6.6 g of NBS and 300 mg of AIBN in 200 ml of $CCl_4$ for 10 h. After cooling, $H_2O$ is added. The phases are separated and the organic phases are dried with $MgSO_4$ and concentrated. Chromatography on $SiO_2$ with EtOAc/cyclohexane (1:4) yields 5.4 g of oil.

MS(EI)=282, 284 (M+) $R_f$[$SiO_2$, EtOAc/cyclohexane (1:4)]=0.38 c) 1-[(2-Ethoxycarbonylbenzo[b]furan-5-yl)methyl]-2-butyl-4-chloro-5-hydroxymethyl-imidazole 1 g (5.3 mmol) of 2-butyl-4-chloro-5-hydroxymethylimidazole (prepared as described in EP-A 253,310) is dissolved in 20 ml of methanol, and a solution of 127 mg of sodium in 5 ml of methanol is added. After 30 min, the mixture is concentrated and dissolved in 40 ml of DMF. 1.5 g (5.5 mmol) of the compound from b) are added and stirred at 25° C. for 14 h. The mixture is poured into 200 ml of H$_2$O and then extracted with EtOAc, and the organic phase is washed with H$_2$O, dried with MgSO$_4$ and concentrated. Chromatography on SiO$_2$ with EtOAc/cyclohexane (1:1) yields 0.73 g of oil.

MS(DCI)=391 (M+ +H) R$_f$ [SiO$_2$; EtOAc/cyclohexane (1:2)]=0.29 d) 1-[(2-Carboxybenzo[b]furan-5-yl)methyl]-2-butyl-4-chloro-5-hydroxymethylimidazole 0.79 g (2.5 mmol) of the compound from c) are boiled under reflux in 20 ml of ethanol with 20 ml of 2N NaOH. After 2 h, the mixture is taken up in water, adjusted to pH 3.5 with 2N HCl and extracted with dichloromethane. Drying and concentration result in 0.31 g of the title compound as an amorphous powder.

MS(DCI)=363 (M+ +H) R$_f$ [SiO$_2$, EtOAc/cyclohexane (1:1)]=0.03

EXAMPLE 2

1-[(2-Carboxybenzo[b]thiophen-5-yl)methyl]-2-butyl-4-chloro-5-hydroxymethylimidazole a) 4-Tolylthioacetaldehyde diethyl acetal 62 g of p-thiocresol in 100 ml of ethanol are added dropwise to a solution of 12.5 g of sodium in 250 ml of ethanol at 0° C. Addition of 15 g of sodium iodide is followed by dropwise addition of 98.5 g of bromoacetaldehyde diethyl acetal and boiling under reflux for 4 h. After cooling, the mixture is poured into 1 l of water and extracted with EtOAc. Drying with MgSO$_4$ is followed by concentration and distillation.

Boiling point 118° (0.01 torr), yield 92.9 g b) 5-Methylbenzo[b]thiophene 320 g of P$_2$O$_5$ are mixed with 246 ml of orthophosphoric acid and heated at 130° C. (1 h) At 180° C., 92.9 g of the compound from a) are introduced by means of a capillary tube under the surface of the polyphosphoric acid at 5 mmHg. The product distils out. 26 g are obtained as an oil.

MS (EI)=135 (M+)

c) 2-Acetyl-5-methylbenzo[b]thiophene

A solution of 26 g of the compound from b) and 13.5 g of acetyl chloride in 250 ml of CH$_2$Cl$_2$ is added dropwise to a suspension of 23.4 g of AlCl$_3$ in 780 ml of CH$_2$Cl$_2$. After 90 min, the dark green solution is poured into ice-cold dilute HCl, and the organic phase is separated off, dried with MgSO$_4$ and concentrated. 25.5 g of product are obtained as an oil.

MS (EI)=178 (M+)

d) 5-Methylbenzo[b]thiophene-2-carboxylic acid 11.7 g of NaOH are dissolved in 58 ml of H$_2$O and, at 10° C., 14.1 g of bromine are added. At 0° C., 5.2 g of 2-acetyl-5-methylbenzo[b]thiophene in 50 ml of dioxane are added. After 90 min, the mixture is acidified with 5N HCl and extracted with CH$_2$Cl$_2$. Drying with Na$_2$SO$_4$ is followed by concentration. Trituration with EtOAc is followed by filtration with suction. 3 g of crystals are obtained.

MS (EI)=192 (M+) R$_f$ [SiO$_2$; CH$_2$Cl$_2$/MeOH (10:1)]=0.37 e) Ethyl 5-methylbenzo[b]thiophene-2-carboxylate 3 g of the compound from d) are boiled under reflux in 2.5N of ethanolic HCl (50 ml) for 2.5 h. Concentration results in 2.27 g of oil.

MS (EI)-220 (M+) R$_f$ [SiO$_2$; CH$_2$Cl$_2$/MeOH (10:1)]=0.82 f) Ethyl 5-bromomethylbenzo[b]thiophene-2-carboxylate 1.77 g of oil are obtained from 2.27 g of the compound from e) and 1.83 g of NBS by the procedure of Example 1b).

MS (EI)=298+300 (M+)

g) 1-[(2-Ethoxycarbonylbenzo[b]thiophen-5-yl)methyl]-2-butyl-4-chloro-5-hydroxymethylimidazole 0.5 g of the title compound is obtained as an oil from 1.1 g of 2-butyl-4-chloro-5-hydroxymethylimidazole and 1.77 g of the compound from f) in analogy to the procedure of Example 1c).

MS(DCI)=407 (M+H) R$_f$ [SiO$_2$; EtOAc/cyclohexane (1:1)]=0.2 h) 1-[(2-Carboxylbenzo[b]thiophen-5-yl)methyl]-2-butyl-4-chloro-5-hydroxymethylimidazole 0.26 g of the title compound, melting point 195° C. (decomposition), is obtained from the compound from g) in analogy to the procedure from Example 1d).

EXAMPLE 3

1-[(2-Carboxyindol-5-yl)methyl]-2-butyl-4-chloro-5-hydroxymethylimidazole a) 30 g (0.189 mol) of p-tolylhydrazine are dissolved in 600 ml of 1N HCl and heated to 40°-50° C. 23 g of ethyl pyruvate are added. After 2 h, the precipitate is filtered off with suction and dried (vacuum). 37 g of product are obtained. MS (EI)=220 (M+)

b) Ethyl 5-methylindole-2-carboxylate 130 g of P$_2$O$_5$ are added to 111 ml of orthophosphoric acid. After cooling, 37 g of the compound from a) are added, and the mixture is heated to 80° C. After the reaction starts, the temperature rises to 130° C. The mixture is cooled and then poured into ice-water and extracted with ethyl acetate. The organic phase is washed with NaHCO$_3$ (1N), H$_2$O and saturated NaCl solution, dried with Na$_2$SO$_4$ and concentrated. The product is recrystallized from n-hexane/EtOAc. 11.7 g of product of melting point 158° C. are obtained.

c) Ethyl 1-acetyl-5-methylindole-2-carboxylate 2.6 g of sodium hydride (50% in oil) are added to 11.7 g of the compound from b) in 100 ml of anhydrous DMF. 4.5 g of acetyl chloride are then added, and the mixture is stirred for 3.5 h. Pouring into H$_2$O is followed by extraction with EtOAc. The organic phase is washed 3× with H$_2$O and 1× with saturated NaCl solution, dried with MgSO$_4$ and concentrated. Chromatography on SiO$_2$ results in 6 g of the title compound as an oil.

MS (EI) 245 (M+) R$_f$ [SiO$_2$; EtOAc/cyclohexane (1:4)]=0.23 d) Ethyl 1-acetyl-5-bromomethylindole-2-carboxylate 3.6 g of the title compound are obtained as an oil from 6 g of the compound from Example 3c) and 4.2 g of NBS in analogy to the procedure of Example 1b).

MS (EI) 323+325 (M+) R$_f$ [SiO$_2$; EtOAc/cyclohexane (1:4)]=0.21 e) 1-[(2-Ethoxycarbonylindol-5-yl)methyl]-2-butyl-4-chloro-5-hydroxymethylimidazole 160 mg of the title compound are obtained as an oil from 0.6 g of 2-butyl-4-chloro-5-hydroxymethylimidazole and 1.1 g of the compound from Example 3d) in analogy to the procedure in Example 1c).

MS (DCI): 390 (M+H+) $R_f$ [SiO$_2$; EtOAc/cyclohexane (1:1)]=0.2 f) 1-[(2-Carboxyindol-5-yl)methyl]-2-butyl-4-chloro-5-hydroxymethylimidazole 40 mg of the title compound are obtained as a resin from 160 mg of the compound from Example 3e) in analogy to the procedure in Example 1d).

MS (DCI) 362 (M+H+) $R_f$ [SiO$_2$; CH$_2$Cl$_2$/MeOH (2:1)]=0.27.

The compounds of Examples 4-11 were synthesized in analogy to Example 1.

These compounds have the following general formula:

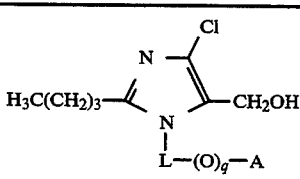

| | MS (DCI; M + H) | A—(O)$_q$—L— |
|---|---|---|
| Example 4 | 413 | |
| Example 5 | 423 | |
| Example 6 | 379 | |
| Example 7 | 407 | |
| Example 8 | 409 | |
| Example 9 | 371 | |

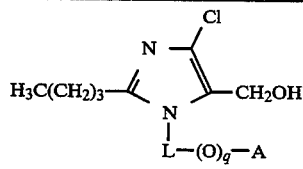

| | MS (DCI; M + H) | A—(O)$_q$—L— |
|---|---|---|
| Example 10 | 439 | |
| Example 11 | 440 | |

3-(5-Methylindol-1-yl)propionitrile (see Example 9)

13 g (0.1 mol) of 5-methylindole are added to 4 ml of trimethylbenzylammonium hydroxide and 10 ml of acrylonitrile in 100 ml of dioxane while stirring. The mixture is then heated at 80° C. for 2 h and subsequently left to stand at room temperature for 3 days. Very dilute acetic acid is then added in order to neutralize the base. Extraction with EA (3×30 ml) is then carried out. The combined organic phases are dried with Na$_2$SO$_4$ and concentrated in vacuo. The residue was chromatographed on SiO$_2$ with DIP as eluent. $R_f$[DIP]=0.3.

Conditions for the esterification of the radicals A in Examples 5, 6 and 7.

20 g of 5-methyl-2,3-dicarboxybenzo[b]thiophene (Example 5) are boiled under reflux in 400 ml of absolute methanol which contains 3% sulfuric acid for 6 h. After cooling to room temperature, the mixture is poured onto ice. The precipitate is filtered off and the H$_2$O phase is extracted 3× with ether. Drying with Na$_2$SO$_4$ is followed by concentration, when the ester results as an oil.

Example 10a)

Alternative to the hydrolysis of the ethyl ester of Example 10 to give the title compound 10

0.5 ml of aqueous 1N NaOH is added to 180 mg (0.38 mmol) of ethyl ester in 2 ml of ethanol, and the mixture is stirred at 25° C. for 20–60 h. It is then concentrated, and the residue is purified on SiO$_2$ with CH$_2$Cl$_2$/MeOH 8:2 as mobile phase, when the acid results as amorphous powder.

EXAMPLE 12

1-[(3-Carboxy-2-phenylimidazo[1,2-a]pyridin-6-yl)methyl]-2-butyl-4-chloro-5-formylimidazole a) 2-Butyl-4-chloro-5-formylimidazole 305 ml of a 1M solution of (NH$_4$)$_2$Ce(NO$_3$)$_6$ in H$_2$O are added slowly at 10°–15° C. to 20 g (0.106 mol) of 2-butyl-4-chloro-5-hydroxymethylimidazole in 350 ml of glacial acetic acid. After 2.5 h at RT, the pH is adjusted to 4 with 2N KOH (20° C. during addition of the base). After extraction 4× with 500 ml of CH$_2$Cl$_2$ each time the combined organic extracts are washed 3× with 300 ml of saturated aqueous NaHCO$_3$ solution each time, dried with Na$_2$SO$_4$ and concentrated, resulting in the title compound as a colorless solid (18 g). Melting point was 90° C.

b) 1-[(3-Ethoxycarbonyl-2-phenylimidazo[1,2-a]pyridin-6-yl)methyl]-2-butyl-4-chloro-5-formylimidazole 0.2 g (1.07 mmol) of 2-butyl-4-chloro-5-formylimidazole, 0.38 g (1.07 mmol) of 6-bromomethyl-3-ethoxycarbonyl-2-phenylimidazo[1,2-a]pyridine, 0.15 g of K$_2$CO$_3$ (1.07 mmol) and 0.5 g of powdered molecular sieves are stirred in 5 ml of DMF at 60° C. for 5 h. Addition of 100 ml of EA is followed by washing 3× with H$_2$O. Drying with Na$_2$SO$_4$ is followed by concentration, and the residue is chromatographed on SiO$_2$ with EA/H 1/1 as eluent.

MS (DCI) 465 (M+H+) R$_f$[SiO$_2$; EA/H (1:1)]=0.18 c) The preparation of the bromomethyl compound from b) and the hydrolysis of the title compound b) is carried out in analogy to Example 1 or 10a.

Example 13 is prepared in analogy to Example 12. These compounds have the following general formula

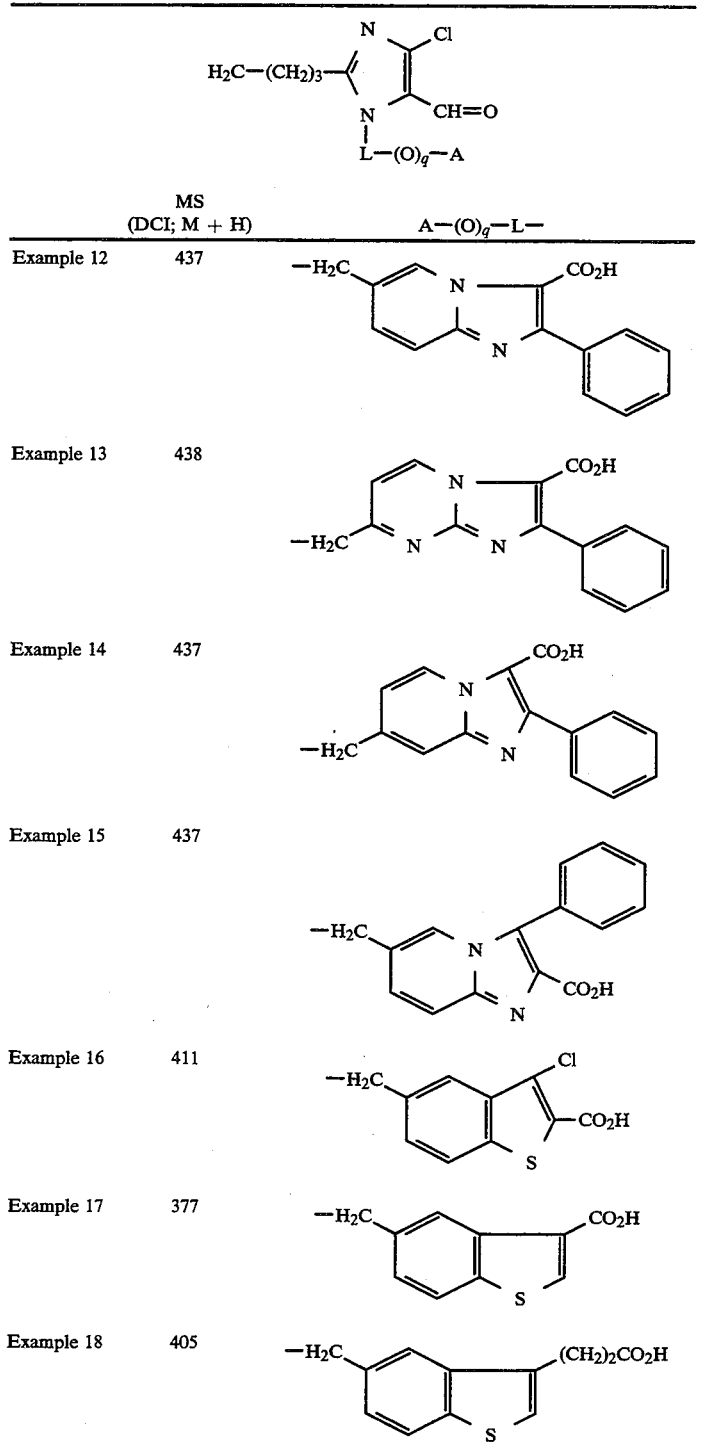

-continued

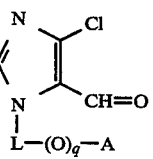

| | MS (DCI; M + H) | A—(O)$_q$—L— |
|---|---|---|
| Example 19 | 449 | 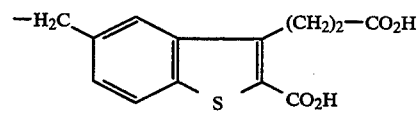 |
| Example 20 | 455 | 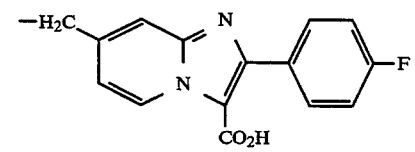 |
| Example 21 | 455 | 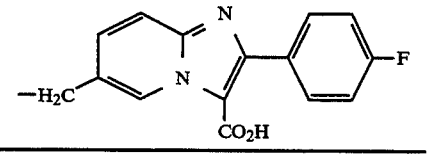 | for Example 15: Preparation of the basic heterocyclic structure

2-Ethoxycarbonyl-3-phenyl-6-methylimidazo[3,2-a]pyridine a) Ethyl phenylpyruvate 13.9 g (0.073 mol) of triethyloxonium tetrafluoroborate are added to 10 g (0.061 mol) of phenylpyruvic acid and 8.6 g (0.073 mol) of diisopropylethylamine in 200 ml of dichloromethane. After 4 h at RT, the organic phase is washed twice with 10% strength citric acid solution and twice with saturated sodium bicarbonate solution. Drying with MgSO$_4$ is followed by concentration. Chromatography on SiO$_2$ with EA/H 1/5 as eluent results in 7 g of an oil.

R$_f$(EA/H 1/5)=0.3 b) Ethyl α-bromophenylpyruvate 2.6 ml of bromine are added to 7 g (0.036 mol) of ethyl phenylpyruvate (a) in 50 ml of tetrachloromethane at 5° C. The mixture is then heated to boiling for 1 h and concentrated, and the residue is taken up in 100 ml of EA. The EA phase is washed twice with 10% strength Na$_2$SO$_3$ solution and once with H$_2$O and dried with MgSO$_4$. Removal of the solvent in vacuo provides 9 g of the compound as oil.

MS (DCI)=271 (M+H)

c) 2-Ethoxycarbonyl-3-phenyl-6-methylimidazo[3,2-a]pyridine 3 g of ethyl α-bromophenylpyruvate (b) and 1.2 g of 2-amino-5-methylpyridine in 50 ml of ethanol are heated to boiling for 2 h. After the alcohol has been stipped off, the residue is taken up in 100 ml of EA. The organic phase is washed once with saturated Na$_2$CO$_3$ solution and then dried with MgSO$_4$. The residue from concentration is chromatographed on SiO$_2$ with EA/H 1/1 as eluent.

Yield: 1.7 g R$_f$(EA/H 1/1)=0.2 MS (DCI)=281

EXAMPLE 22

1-[2-(5-Tetrazolyl)-3-chlorobenzo[b]thiophen-6-ylmethyl]-2-n-butyl-4-chloro-5-hydroxymethylimidazole a) 3-Chloro-6-methylbenzo[b]thiophene-2-carboxamide 100 ml of 4N NH$_3$ in DME are added dropwise to 30 g (12.3 mmol) of 3-chloro-6-methylbenzo[b]thiophene-2-carbonyl chloride (J. Org. Chem. 41, 3399, (1976) in dimethoxyethane at 0° C. After 30 min, the mixture is concentrated and the title compound is crystallized from ethanol, resulting in 14.5 g.

Melting point: =193° C. R$_f$ (EA/H 1/1)=0.3 MS (DCI)=226 (M+H)

b) 3-Chloro-2-cyano-6-methylbenzo[b]thiophene 6.2 g (53.2 mmol) of thionyl chloride are added to 3 g (13.3 mmol) of title compound a) in 40 ml of pyridine at 0° C. After 2 h, the mixture is poured onto ice-cold 4N HCl and extracted 3 times with 50 ml of EA each time. The combined organic phases are dried with MgSO$_4$ and concentrated. Chromatography on SiO$_2$ with EA/H ½ provides the title compound (1.5 g).

R$_f$(EA/H 1/1)=0.75 MS (DCI)=208 (M+H)

c) 1-[2-(5-Tetrazolyl)-3-chlorobenzo[b]thiophen-6-ylmethyl]-2-n-butyl-4-chloro-5-hydroxymethylimidazole 0.4 g (1.0 mmol) of 1-[(2-cyano-3-chlorobenzo[b]thiophen-6-yl)methyl]-2-n-butyl-4-chloro-5-hydroxymethylimidazole (prepared from 22 b in analogy to Example 1b, c) and 0.42 g (2.0 mmol) trimethyltinazid in 50 ml of toluene are heated to boiling for 24 h. The mixture is then concentrated and the residue is taken up in 20 ml of EA and, at RT, 0.6 ml of HBF$_4$ and 15 ml of saturated KF solution are added. After 12 h, a further 20 ml of EA are added, and the phases are separated. The organic phase is dried with MgSO$_4$ and concentrated. Chromatography on SiO$_2$ with dichloromethane/methanol 5/1 provides the title compound.

R$_f$(CH$_2$Cl$_2$/MeOH 5/1)=0.4 MS (FAB)=437

EXAMPLE 23

1-[(2-phenyl-3-carboxyimidazo[1,2-a]pyrimidin-7-yl)-methyl]-2-n-butyl-4-methylthioimidazole-5-carboxylic acid a) Ethyl 2-amino-2-cyanoacetate 119 g of sodium dithionite are added in portions (15 min) to 35 g (0.246 mol) of ethyl 1-cyanoglyoxylate 2-oxime in 350 ml of $H_2O$ and 280 ml of saturated sodium bicarbonate solution at room temperature. The mixture is subsequently heated at 35° C. for 1 hour; then saturated with NaCl and extracted 5× with dichloromethane. After drying with calcium chloride, the organic phase is concentrated. 11.8 g of the title compound are obtained as an oil.

$R_f(CH_2Cl_2/CH_3OH\ 9/1)=0.6$ b) Ethyl 2-cyano-2-n-butylcarbonylaminoacetate 3.39 ml (28.09 mmol) of valeroyl chloride in 5 ml of $CH_2Cl_2$ are added dropwise to 3.6 g (28.09 mmol) of compound 23a) in 50 ml of dry $CH_2Cl_2$ and 2.3 ml (28.09 mmol) of pyridine at $-5°$ C. to $0°$ C. The mixture is then stirred at room temperature for 1 hour. The organic phase is then washed 3 times with $H_2O$ and once with saturated NaCl solution, dried with calcium chloride and concentrated. Crystallization from DIP provides 1.7 g of the title compound.

$R_f(CH_2Cl_2/CH_3OH\ 9/1)=0.35$ Melting point: 87° C.

c) Ethyl 3-amino-2-n-butylcarbonylaminomethylthioacrylate 2 ml (27.26 mmol) of condensed methyl mercaptan are added to 2.9 g (13.67 mmol) of compound 23b) and 0.19 ml (1.36 mmol) of triethylamine in 60 ml of absolute ethanol at room temperature. After 3 days, a further 0.5 ml of methyl mercaptan is added. After a further 24 hours at room temperature, a further 0.5 ml of methyl mercaptan and 0.19 ml of triethylamine are injected in, and the mixture is stirred at room temperature for a further 24 hours. The solvent is then removed and the residue is crystallized from DIP, resulting in 2.4 g of the title compound.

$R_f(CH_2Cl_2/EA\ 4/1)=0.3$ Melting point: 120° C.

d) Ethyl 2-n-butyl-4-methylthioimidazole-5-carboxylate 2.44 g (20.0 mmol) of 4-dimethylaminopyridine in 12 ml of $CH_2Cl_2$ are added dropwise to 4.17 g (20.0 mmol) of phosphorus pentachloride in 20 ml of $CH_2Cl_2$ at $-78°$ C. After 5 min, 2.42 g (10.0 mmol) of compound 23c) in 25 ml of $CH_2Cl_2$ are added dropwise. The mixture is then allowed to reach room temperature and is diluted with 30 ml of $CH_2Cl_2$. After 2 hours, 300 ml of 1N sodium bicarbonate solution are added while cooling in ice, and the mixture is stirred for 1 hour. The phases are then separated, the aqueous phase is extracted 3 times with EA, and the combined organic phases are dried with calcium chloride. Chromatography on $SiO_2$ with $CH_2Cl_2/EA$ (9/1) provides 1.4 g of the title compound as an oil.

$R_f(CH_2Cl_2/EA\ 9/1)=0.6$ MS (DCI)=243 (M++H)

The remaining reaction steps to the title compound 23 are carried out in analogy to Example 12b), 1b) and 10a.

$R_f(EA/MeOH\ 5/1)=0.2$ MS (FAB)=466 (M+H)

EXAMPLE 24

1-[(2-Phenyl-3-carboxyimidazo[1,2-a]pyrimidin-7-yl)methyl]-2-n-butyl-4-methylsulfinylimidazole-5-carboxylic acid a) Ethyl 1-[(2-phenyl-3-carboxyethylimidazo[1,2-a]pyrimidin-7-yl)methyl]-2-n-butyl-4-methylsulfinylimidazole-5-carboxylate 52 mg (0.15 mmol) of 50% pure metachloroperbenzoic acid are added at room temperature to 80 mg (0.15 mmol) of ethyl 1-[(2-phenyl-3-carboxyethylimidazo[1,2-a]pyrimidin-7-yl)methyl]-2-n-butyl-4-methylthioimidazole carboxylate in 5 ml of dichloromethane. After 1 h, the mixture is washed once with saturated $Na_2CO_3$ solution and once with $H_2O$. The organic phase is concentrated, and the residue provides after chromatography on $SiO_2$ with EA/H 1/1 as eluent the title compound.

$R_f(EA/H\ 1/1)=0.15$ MS (FAB)=538 (M+H)

b) The title compound 24 is obtained in analogy to Example 10a).

$R_f\ (CH_2Cl_2/MeOH\ 5/1)=0.2$ MS (FAB)=482 (M+H)

EXAMPLE 25

1-[(2-Phenyl-3-carboxyimidazo[1,2-a]pyrimidin-7-yl)methyl]-2-n-butyl-4-methylsulfonylimidazole-5-carboxylic acid a) 158 mg (0.46 mmol) of 50% pure metachloroperbenzoic acid are added to 120 mg (0.23 mmol) of ethyl 1-[(2-phenyl-3-carboxyethylimidazo[1,2-a]pyrimidin-7-yl)methyl]-2n-butyl-4-methylthioimidazole-5-carboxylate in 10 ml of dichloromethane at RT. Further course of the reaction and working as 24a).

$R_f(EA)=0.6$ MS (FAB)=554 (M+H)

b) The hydrolysis to give the title compound is carried out in analogy to Example 10a). $R_f\ (CH_2Cl_2/MeOH\ 5/1)=0.2$ MS (FAB)=498 (M+H)

Examples 26 and 27 are prepared in analogy to Examples 24 and 25.

Examples 28-33 are prepared in analogy to Example 22.

Preparation of 2-phenyl-3-amido-7-methylimidazo[1,2-a]pyrimidine (for Example 28): 500 mg (1.78 mmol) of 2-phenyl-3-carbethoxy-7-methylimidazo[1,2-a]pyrimidine, 213 μl (5.35mmol) formamide and 120 mg of potassium tertiary-butylate in 10 ml of DMF are heated at 100° C. for 1 h. The mixture is then poured into $H_2O$, the pH is adjusted to 8-9 with $NaHCO_3$, and filtration with suction is carried out.

$R_f(EA)=0.3$ MS (DCI)=252 (M+H)

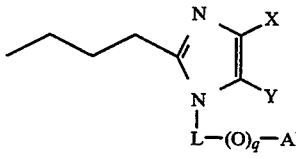

| | MS (FAB; M + H) | X | Y | A—(O)$_q$—L |
|---|---|---|---|---|
| Example 22 | 437 | Cl | CH$_2$—OH | 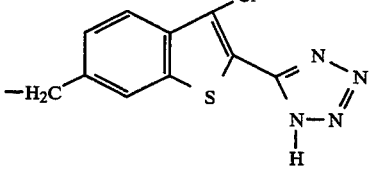 |
| Example 23 | 466 | —S—CH$_3$ | CO$_2$H | 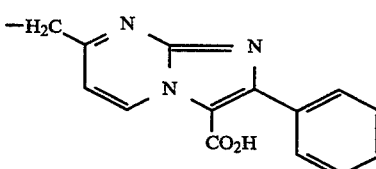 |
| Example 24 | 482 | —SOCH$_3$ | CO$_2$H | |
| Example 25 | 498 | —SO$_2$CH$_3$ | CO$_2$H | |
| Example 26 | 455 | —SOCH$_3$ | CO$_2$H | 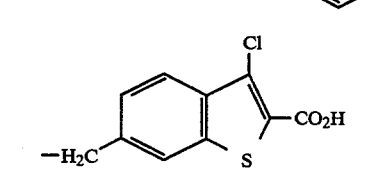 |
| Example 27 | 471 | —SO$_2$CH$_3$ | CO$_2$H | |
| Example 28 | 517 | —S—CH$_3$ | CO$_2$Et | 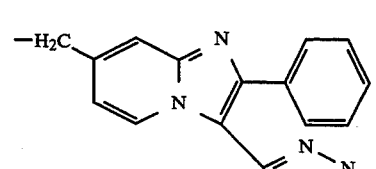 |
| Example 29 | 488 | —S—CH$_3$ | CO$_2$H | |
| Example 30 | 497 | —S—CH$_3$ | CO$_2$Et | 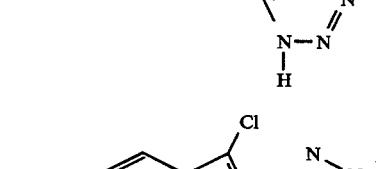 |
| Example 31 | 463 | —SCH$_3$ | CO$_2$H | |
| Example 32 | 523 | —SO$_2$CH$_3$ | CO$_2$Et | |
| Example 33 | 495 | —SO$_2$CH$_3$ | CO$_2$H | |

Example 34

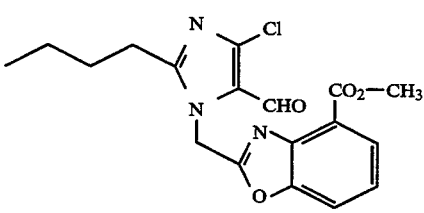

1-[(2-(4-methoxycarbonyl)benzoxazolyl)methyl]-2-n-butyl-4-chloro-5-formylimidazole a) Methyl 2-bromomethylbenzoxazole-4-carboxylate 453 mg (2.37 mmol) of methyl 2-methylbenzoxazole-4-carboxylate (prepared by the method in J. Heterocyclic Chem. 27, 335 (1990)) are dissolved in 40 ml of chlorobenzene, 421 mg (2.37 mmol) of NBS and 20 mg of benzoyl peroxide are added, and the resulting mixture is refluxed for 2 hours. It is concentrated, and the residue is taken up in ethyl acetate, extracted by shaking with saturated NaHCO$_3$, 10% strength Na$_2$SO$_3$ and saturated NaCl solution and dried over Na$_2$SO$_4$. Concentration and chromatography on SiO$_2$ with n-heptane-ethyl acetate (2:1) yields 128 mg of the title compound.

Melting point: 110°–113° C. MS (CI)=271 (M+H)

b) 1-[(2-(4-methoxycarbonyl)benzoxazolyl)methyl]-2-n-butyl-4-chloro-5-formylimidazole A solution of 255 mg (0.944 mmol) of the compound from a) in 1 ml of absolute DMF is added dropwise to a suspension of 176 mg (0.944 mmol) of 2-n-butyl-4-chloro-5-formylimidazole and 130 mg (0.944 mmol) of K$_2$CO$_3$ in 2 ml of absolute DMF, and the resulting suspension is stirred at RT for 1 hour. It is evaporated to dryness, and the residue is taken up in ethyl acetate, washed with water and saturated in HCl solution, dried and concentrated. Chromatography on $SiO_2$ with $CH_2Cl_2$/ethyl acetate (9:1) yields 103 mg of the required compound,

MS (CI)=376 (M+H)

EXAMPLE 35

1-[(2-(5-methoxycarbonyl)benzoxazolyl)methyl]-2-n-butyl-4-chloro-5-formylimidazole a) Methyl 2-bromomethylbenzoxazole-5-carboxylate The title compound is prepared from methyl 2-methylbenzoxazole-5-carboxylate by the process indicated in Example 14a),

MS (CI)=271 (M+H)

b) 1-[(2-(5-Metrhoxycarbonyl)benzoxazolyl)methyl]-2-n-butyl-4-chloro-5-formylimidazole This compound is prepared from the Compound from a) and 2-n-butyl-4-chloro-5-formylimidazole by the process of Example 34b),

MS (CI)=376 (M+H)

We claim:

1. A compound of the formula I

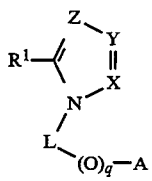

in which

Z is N;

X and Y are identical or different and are $CR^2$;

$R^1$ is $(C_3-C_7)$-alkyl, $(C_3-C_7)$-alkenyl or $(C_3-C_7)$-alkynyl;

$R^2$ is independently chlorine, bromine, $-S(O)_rR^6$, $-COR^8$, or $(C_1-C_6)$-alkyl substituted by hydroxyl;

$R^3$ is independently hydrogen or $(C_1-C_4)$-alkyl;

$R^5$ is independently hydrogen, $(C_1-C_6)$-alkyl, $(C_3-C_8)$-cycloalkyl, phenyl, or benzyl;

$R^6$ is independently hydrogen, $(C_1-C_4)$-alkyl, $(C_1-C_4)$-alkanoyl, or $(C_6-C_{12})$-aryl, wherein $(C_6-C_{12})$-aryl is unsubstituted or substituted by 1 or 2 identical or different radicals selected from halogen, hydroxyl, methoxy, nitro, cyano, $CO_2R^3$ and trifluoromethyl;

$R^7$ is independently hydrogen, $(C_1-C_4)$-alkyl, or $(C_6-C_{12})$-aryl-$(C_1-C_4)$-alkyl;

$R^8$ is independently hydrogen, $(C_1-C_4)$-alkyl, $OR^5$ or morpholino;

A is a fused heterobicyclic radical selected from a radical of benzothiophene, benzofuran, indole, isoindole, indazole, benzimidazole, quinoline, isoquinoline, phthalazine, quinoxaline, quinazoline, cinnoline, benzothiazole, benzothiazole-1,1-dioxide, coumarin, chroman, benzoxazole, benzisothiazole, benzodiazines, benzotriazole, benzotriazine, benzoxazine, imidazopyridine, imidazopyrimidine, imidazopyrazine, imidazopyridazine, imidazothiazole, pyrazolopyridine, thienopyridine and pyrrolopyrimidine, which is unsubstituted or substituted by up to 3 identical or different radicals $R^{14}$ or $-(CH_2)_{n-1}-(CHR^6-CH_2)_{o-1}-R^{15}$;

$R^{14}$ is independently $(C_1-C_4)$-alkyl, $(C_1-C_4)$-alkoxy, cyano, amino, nitroso, nitro, fluorine, chlorine, bromine, hydroxyl, $CH_2OR^7$, $(C_1-C_4)$-alkanoyloxy, $(C_1-C_4)$-alkanoyl, benzoyl, $-NH-CO-R^7$ or tetrazolyl;

$R^{15}$ is independently $(C_6-C_{12})$-aryl, cyano, chlorine, bromine, $-CO_2R^3$, or $(C_6-C_{12})$-aryl which is substituted by 1 or 2 identical or different radicals selected from halogen, cyano, nitro, $NR^6R^7$ and hydroxyl;

L is $(C_1-C_3)$-alkanediyl;

n is independently 1 or 2;

o is independently 1 or 2;

q is 0 or 1;

r is independently 0, 1 or 2, or a physiologically tolerated salt thereof.

2. A compound of the formula I or a physiologically tolerated salt thereof as claimed in claim 1, in which A is a radical selected from a radical of benzoxazole, benzothiophene, imidazopyridine, imidazopyrimidine, benzofuran, and indole, which is unsubstituted or substituted by up to 3 identical or different radicals $R^{14}$ or $-(CH_2)_{n-1}-(CHR^6-CH_2)_{o-1}-R^{15}$.

3. A compound of the formula I or a physiologically tolerated salt thereof as claimed in claim 2 in which $R^2$ is independently chlorine, bromine, $-S(O)_rR^6$, or $-COR^8$;

$R^{14}$ is independently tetrazolyl;

$R^{15}$ is independently $-CO_2R^3$;

q is zero; and

L is $CH_2$.

4. A compound of the formula I or a physiologically tolerated salt thereof as claimed in claim 1 in which $R^2$ is independently chlorine bromine $-S(O)_rR^6$, or $-COR^8$;

$R^{14}$ is independently tetrazolyl;

$R^{15}$ is independently $-CO_2R^3$;

q is zero; and

L is $CH_2$.

5. A pharmaceutical composition for the treatment of high blood pressure which comprises a pharmaceutically effective amount for said treatment of a compound of the formula I or a physiologically tolerated salt thereof as claimed in claim 1, together with a pharmaceutically acceptable carrier.

6. A method for the treatment of high blood pressure which comprises administering to a host in recognized need of said treatment a pharmaceutical composition as claimed in claim 5.

7. A method for the treatment of high blood pressure which comprises administering to a host in recognized need of said treatment a pharmaceutically effective amount of a compound of the formula I or a physiologically tolerated salt thereof as claimed in claim 1.

8. A pharmaceutical composition for the treatment of high blood pressure which comprises a pharmaceutically effective amount for said treatment of a compound of the formula I or a physiologically tolerated salt thereof as claimed in claim 4, together with a pharmaceutically acceptable carrier.

9. A pharmaceutical composition for the treatment of high blood pressure which comprises a pharmaceutically effective amount for said treatment of a compound of the formula I or a physiologically tolerated salt thereof as claimed in claim 3, together with a pharmaceutically acceptable carrier.

10. A pharmaceutical composition for the treatment of high blood pressure which comprises a pharmaceutically effective amount for said treatment of a compound of the formula I or a physiologically tolerated salt thereof as claimed in claim 2, together with a pharmaceutically acceptable carrier.

11. A method for the treatment of high blood pressure which comprises administering to a host in recognized need of said treatment a pharmaceutical composition as claimed in claim 10.

12. A method for the treatment of high blood pressure which comprises administering to a host in recognized need of said treatment a pharmaceutical composition as claimed in claim 9.

13. A method for the treatment of high blood pressure which comprises administering to a host in recognized need of said treatment a pharmaceutical composition as claimed in claim 8.

14. A method for the treatment of high blood pressure which comprises administering to a host in recognized need of said treatment a pharmaceutically effective amount of a compound of the formula I or a physiologically tolerated salt thereof as claimed in claim 4.

15. A method for the treatment of high blood pressure which comprises administering to a host in recognized need of said treatment a pharmaceutically effective amount of a compound of the formula I or a physiologically tolerated salt thereof as claimed in claim 3.

16. A method for the treatment of high blood pressure which comprises administering to a host in recognized need of said treatment a pharmaceutically effective amount of a compound of the formula I or a physiologically tolerated salt thereof as claimed in claim 2.

17. A compound of the formula I

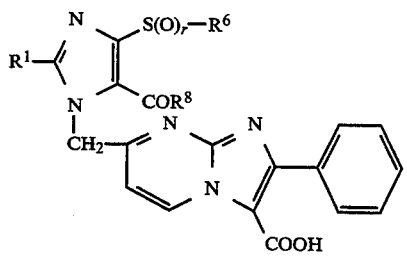

in which
$R^1$ is —$CH_2CH_2CH_2CH_3$;
r is 0, 1, or 2;
$R^6$ is ($C_1$-$C_4$)-alkyl;
$R^8$ is hydrogen or —$OR^5$; and
$R^5$ is hydrogen or ($C_1$-$C_6$)-alkyl,
or a physiologically tolerated salt thereof.

18. A pharmaceutical composition for the treatment of high blood pressure which comprises a pharmaceutically effective amount for said treatment of a compound of the formula I or a physiologically tolerated salt thereof as claimed in claim 17, together with a pharmaceutically acceptable carrier.

19. A method for the treatment of high blood pressure which comprises administering to a host in recognized need of said treatment a pharmaceutical composition as claimed in claim 18.

20. A method for the treatment of high blood pressure which comprises administering to a host in recognized need of said treatment a pharmaceutically effective amount of a compound of the formula I or a physiologically tolerated salt thereof as claimed in claim 17.

* * * * *